United States Patent
Kinnari et al.

[11] Patent Number: 6,022,755
[45] Date of Patent: Feb. 8, 2000

[54] REGENERATION OF FISCHER-TROPSCH CATALYSTS BY USING SYNTHESIS GAS AT A LOW FLOW RATE

[75] Inventors: Keijo J. Kinnari, Sola; Dag Schanke, Trondheim, both of Norway

[73] Assignee: Den norske stats oljeselskap a.s., Stavander, Norway

[21] Appl. No.: 08/945,536

[22] PCT Filed: Apr. 2, 1996

[86] PCT No.: PCT/NO96/00075

§ 371 Date: Jan. 27, 1998

§ 102(e) Date: Jan. 27, 1998

[87] PCT Pub. No.: WO96/31276

PCT Pub. Date: Oct. 10, 1996

[30] Foreign Application Priority Data

Apr. 7, 1995 [GB] United Kingdom ............... 9507271

[51] Int. Cl.[7] .................................................. H01L 21/00
[52] U.S. Cl. .................................. 438/53; 438/56; 438/34
[58] Field of Search ................... 502/34, 53, 56

[56] References Cited

U.S. PATENT DOCUMENTS

| | | | |
|---|---|---|---|
| 3,754,993 | 8/1973 | Oguchi et al. | 134/25 |
| 3,826,739 | 7/1974 | Kubo et al. | 208/157 |
| 3,915,840 | 10/1975 | Gladrow et al. | 208/70 |
| 5,157,054 | 10/1992 | Herbolzheimer et al. | 518/700 |
| 5,260,239 | 11/1993 | Hsia | 502/30 |
| 5,268,344 | 12/1993 | Pedrick et al. | 502/30 |
| 5,283,216 | 2/1994 | Mitchell | 502/30 |

FOREIGN PATENT DOCUMENTS

94/14537   7/1994   WIPO.

*Primary Examiner*—Jey Tsai
*Assistant Examiner*—Alexander G. Ghyka
*Attorney, Agent, or Firm*—Kirkpatrick & Lockhart LLP

[57] ABSTRACT

A method of regenerating the catalyst in a Fischer-Tropsch synthesis reaction. Synthesis gas is supplied to the catalyst in conditions which favor high CO conversions. This results in a high $H_2$ partial pressure which in turn results in catalyst regeneration.

25 Claims, 2 Drawing Sheets

REGENERATION OF FISCHER-TROPSCH CATALYSTS BY USING SYNTHESIS GAS AT A LOW FLOW RATE

BACKGROUND OF THE INVENTION

The present invention relates to the regeneration of Fischer-Tropsch (F-T) catalysts, in particular, the finely divided solid catalyst used when the F-T reaction is carried out in slurry reactors.

The F-T synthesis is carried out in various types of slurry reactors, one example being bubble column reactors. The operation of bubble column slurry reactors is flexible. They combine low diffusional resistance with efficient heat transfer. Examples of bubble column reactors used for F-T synthesis are shown in the present Applicants' WO 93/16796, WO 93/16795, WO 94/16807 and British Patent Application No. 9317605.5. Mechanically agitated slurry reactors are particularly convenient for laboratory studies due to the low mass-transfer and heat resistance. These features make them suitable for the determination of reaction kinetics. However, this technique is generally of minor importance on an industrial scale.

The reaction products are a complicated mixture, but the main reaction can be illustrated by the following equation:

$$nCO + 2nH_2 \rightarrow (-CH_2-)_n + nH_2O \quad (I)$$

where ($-CH_2-$) represents a straight chain hydrocarbon of carbon number n. The carbon number refers to the number of carbon atoms making up the main skeleton of the molecule. In F-T synthesis, the products are generally either paraffins, olefins, or alcohols. Products range in carbon number from 1 to 50 or higher.

The common F-T catalysts are nickel, cobalt, and iron. Nickel was probably the first substance to be recognised as capable of catalysing the reaction of syngas to hydrocarbons, producing mainly methane. Iron and cobalt are able to produce higher chain hydrocarbons and are, thus, preferred as catalysts for the production of liquid hydrocarbons. However, other metals are also capable of catalysing the conversion of syngas.

In recent years considerable advances have been made in the development of F-T catalysts and much of this work is well documented in the art. As far as slurry reactors are concerned, suitable catalysts are disclosed in EP-A-313375 and in the present Applicants' EP-A-404902. The latter reference describes broadly a cobalt catalyst which is composited on an alumina support together with rhodium, and platinum and/or iridium. The production of hydrocarbons by the F-T synthesis method, using cobalt-based catalysts can result in catalyst deactivation. This may be caused by various undesirable phenomena, such as re-oxidation of the active metal.

There are several known regeneration methods. These generally fall into two categories, namely, oxidative and reductive. In oxidative regeneration, the catalyst is removed from the slurry environment after which a treatment with air or oxygen is carried out to burn away the hydrocarbon rests. This is followed by normal catalyst activation. In reductive regeneration, the catalyst can be activated in-situ using hydrogen. Different systems can be used to achieve this, such as are described in U.S. Pat. Nos. 5,260,239 and 5,268,344, for regeneration in a slurry reactor.

In U.S. Pat. No. 5,260,239 a system is described in which there is a reaction vessel and a regeneration vessel. There is a mutual exchange of the catalyst slurry between the vessels by way of downcomers and $H_2$ gas is injected into the rejuvenation vessel to regenerate the catalyst.

In U.S. Pat. No. 5,268,344, the reactor vessel itself contains vertical tubes open at both ends. $H_2$ gas is injected into the bottom of the tubes which has the effect of drawing slurry up the tubes and while in the tubes, regenerating the catalyst.

These arrangements all suffer the drawback that a separate source of $H_2$ gas must be provided to achieve regeneration.

SUMMARY OF THE INVENTION

It is an object of the present invention to provide a system for regenerating an F-T catalyst which does not suffer from this drawback of the prior art systems.

According to the invention, there is provided a method for the regeneration of a solid particulate catalyst used in the synthesis of hydrocarbons from synthesis gas in a reaction zone, the method comprising: adjusting the feed parameters of the synthesis gas to increase conversion of CO in the synthesis gas until the $H_2/CO$ ratio of the gas leaving the reaction zone exceeds a regeneration mode level of 10:1; maintaining the conversion in the regeneration mode for a period of time in order to reach a predetermined degree of regeneration: and then readjusting the feed parameters for normal operation of the synthesis reaction.

Preferably, the $H_2$:CO ratio is greater than 20:1, and more preferably, greater than 30:1.

Preferably, the CO conversion rate is at least 80%, more preferably at least 90%, even more preferably between 95% and 100%, and most preferably, complete.

The increase in CO conversion can conveniently be achieved by reducing, preferably gradually, the synthesis gas flow rate. In this way it is not necessary to shut down the supply of synthesis gas and replace it with hydrogen, as has been the case in prior art systems, nor indeed to employ a dedicated hydrogen supply.

An alternative would be to increase the proportion of hydrogen in the synthesis gas feed. This could be achieved, for example, by adjusting the operating conditions of the reformer, from which the synthesis gas feed would be obtained. A further alternative would be to increase the reaction temperature until the CO conversion rate and the $H_2$:CO ratio meet the criteria defined above.

It has been found that at a high enough CO conversion, the synthesis changes from the Fischer-Tropsch synthesis mode to regeneration mode. The characteristics of this mode are an almost complete CO conversion, high $H_2/CO$ ratio, high $CO_2$ selectivity and low $C_{5+}$ selectivity. This indicates a high water gas shift (WGS) rate which increases due to the low CO partial pressures at high CO conversion. The resulting effect of the new reaction mode is a regenerative gas mixture. The in situ production of this at the catalytic surface is believed to have a positive effect in obtaining the desired result.

The water gas shift reaction may be represented by $$CO + H_2O \rightarrow H_2 + CO_2 \quad (II)$$

In one possible system, the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

The reactor would be allowed to run in the regenerative mode for a short period of time. Experimentally, it has been found out that a few hours operation is sufficient, but the exact time will depend on the degree of deactivation.

The exact conditions from the FT mode to the regeneration mode would take place, would be greatly dependent on the specific system properties such as catalyst specification (type, size, metal loading etc), catalyst loading (ie. catalyst concentration) and reaction conditions. However, when in a commercial operation, ie. high conversion and maximum $C_{5+}$ selectivity, the conversion level is increased, there is a clear drop in the $C_{5+}$ selectivity due to the increased water gas shift reaction and an increase in production of light hydrocarbons, especially methane. This could be used as a criterion for entering the regeneration mode. Another parameter to use as a criterion for changing to the regeneration mode might be the exit $H_2/CO$ ratio. Preferably, this would have to be above 10:1, more preferably 20:1, even more preferably above 30:1. This may be preferable to selectivity as a criterion parameter.

In another possible system, the synthesis reaction is carried out in a reaction vessel and a separate regeneration vessel is provided, the vessels being interconnected to allow a slurry of the catalyst and hydrocarbon product to flow from the reaction vessel to regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

Preferably, there is a continuous flow of a slurry containing the deactivated catalyst, from synthesis reactor to the regeneration unit, and of a slurry containing the regenerated and partly non-regenerated catalyst, back to the synthesis reactor.

Preferably, the regeneration is carried out by operating the vessel at a complete CO conversion (close to 100%) using a typical Fischer-Tropsch feed. If desired, the $H_2/CO$ ratio can be increased but this should not be necessary. The unit can be designed so that the desired conversion level is obtained with almost any $H_2/CO$ ratio of commercial interest for a Co based catalyst. The degree of regeneration can be controlled by the slurry residence time in the regeneration vessel.

In another possible system, the synthesis is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

Preferably, after complete regeneration, the content of the regeneration vessel is brought back to the FT reactor. This operation mode offers a uniform degree of regeneration of all the catalyst, not a distribution as in the continuous case. In addition, the selection of the regeneration time is more flexible than in the continuous case where longer residence time requires larger vessel size and/or reduced slurry throughput rate.

The invention also extends to methods of conducting an F-T synthesis reaction incorporating the methods of regeneration described above.

BRIEF DESCRIPTION OF THE DRAWINGS

The invention may be carried into practice in various ways and some embodiments will now be described by way of example with reference to the accompanying drawings, in which.

DETAILED DESCRIPTION OF THE INVENTION

Figure 1:
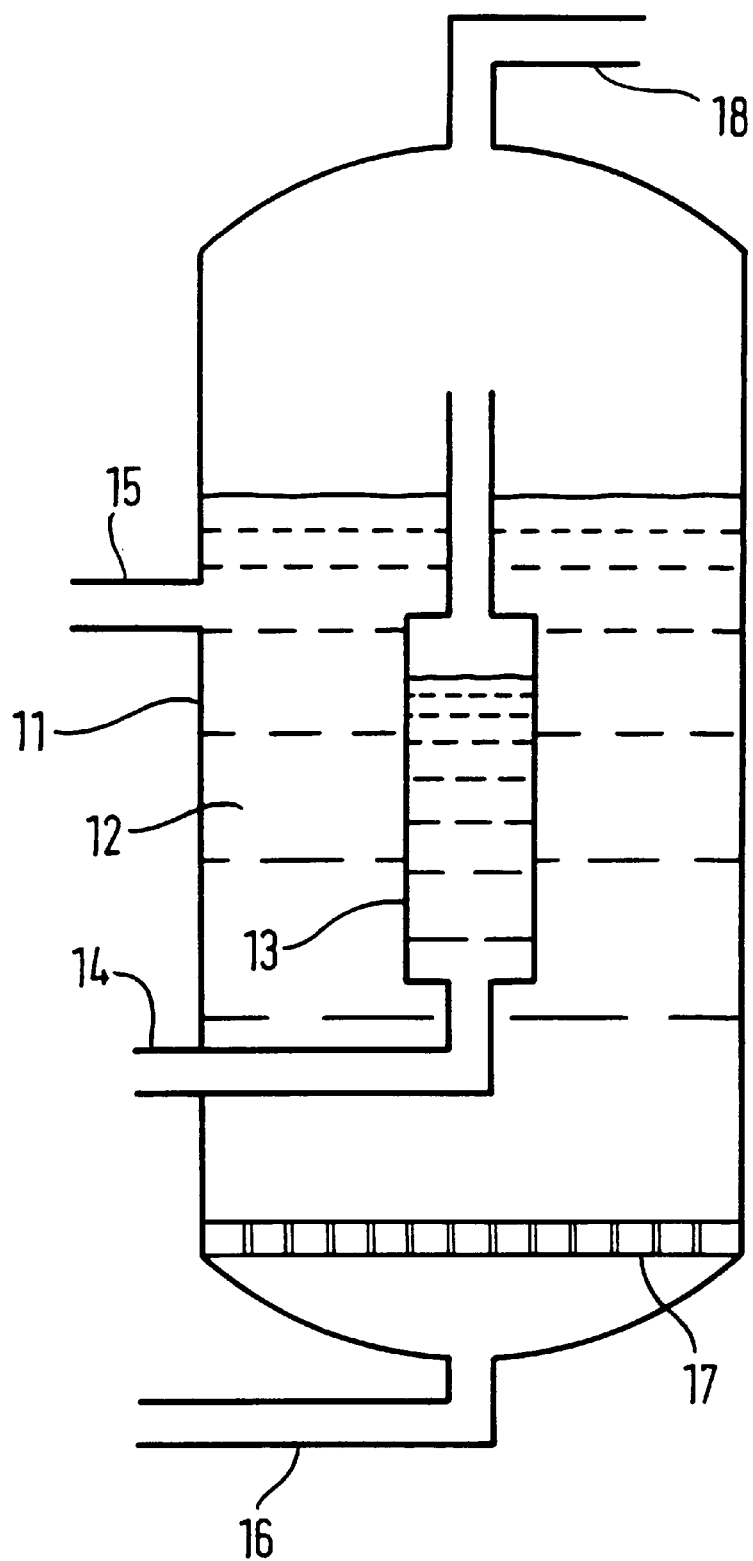
FIG. 1 is a schematic section through a slurry reactor.

The slurry reactor in FIG. 1 is merely a schematic representation and comprises a reaction vessel 11 containing a slurry 12 of finely divided solid catalyst in a liquid hydrocarbon which is the desired product of a Fischer-Tropsch synthesis. A product separator 13 is located within the slurry having a product outlet 14. The reaction vessel 11 has a slurry inlet 15, a feed gas inlet 16 at the bottom beneath a gas distribution device 17, and a gas outlet 18 at the top.

In the normal F-T synthesis mode, synthesis gas, comprising hydrogen and carbon monoxide in a molar ratio of close to 2:1 $H_2$: CO is supplied in the inlet 16. The distribution device 17 causes the synthesis gas to enter the slurry 12 as fine streams of bubbles which act to keep the slurry 12 in a constant state of agitation.

The $H_2$ and CO react to produce the desired hydrocarbon product which is separated by the separator 13 and removed via the outlet 14. Excess synthesis gas is removed via the outlet 18 and recycled, optionally after treatment to remove entrained material.

When the activity of the catalyst diminishes beyond a particular level, the system is switched to regeneration mode. The criteria used to determine when to switch modes will depend upon the particular plant and the particular operator. One operator may chose to switch to regeneration mode when the conversion rate or the selectivity have decreased to a predetermined level, e.g. to 80% of the maximum rate or selectivity, and another operator may choose to switch to the regeneration mode on a regular basis, e.g. every third or fifth day of continuous operation. In regeneration mode, the supply of synthesis gas at 16 is modified in such a way that the synthesis reaction tends towards complete CO conversion. This can be achieved by reducing the feed rate and/or increasing the reaction temperature, or by some other means. At a sufficiently high CO conversion rate, the $H_2/CO$ ratio increases, so producing regenerative conditions.

The required time for maintaining the regeneration mode will depend on several factors. These include the initial degree of deactivation, the required level of re-activation, the gas flow rate in relation to the amount of catalyst present, the catalyst particle size, and the reaction temperature. In practice, a regeneration time of anything between 4 and 36 hours might be necessary though more commonly, a time of from 12 to 24 hours might be appropriate.

After regeneration, the synthesis gas feed conditions are returned to normal and the F-T synthesis resumes and continues.

Figure 2:
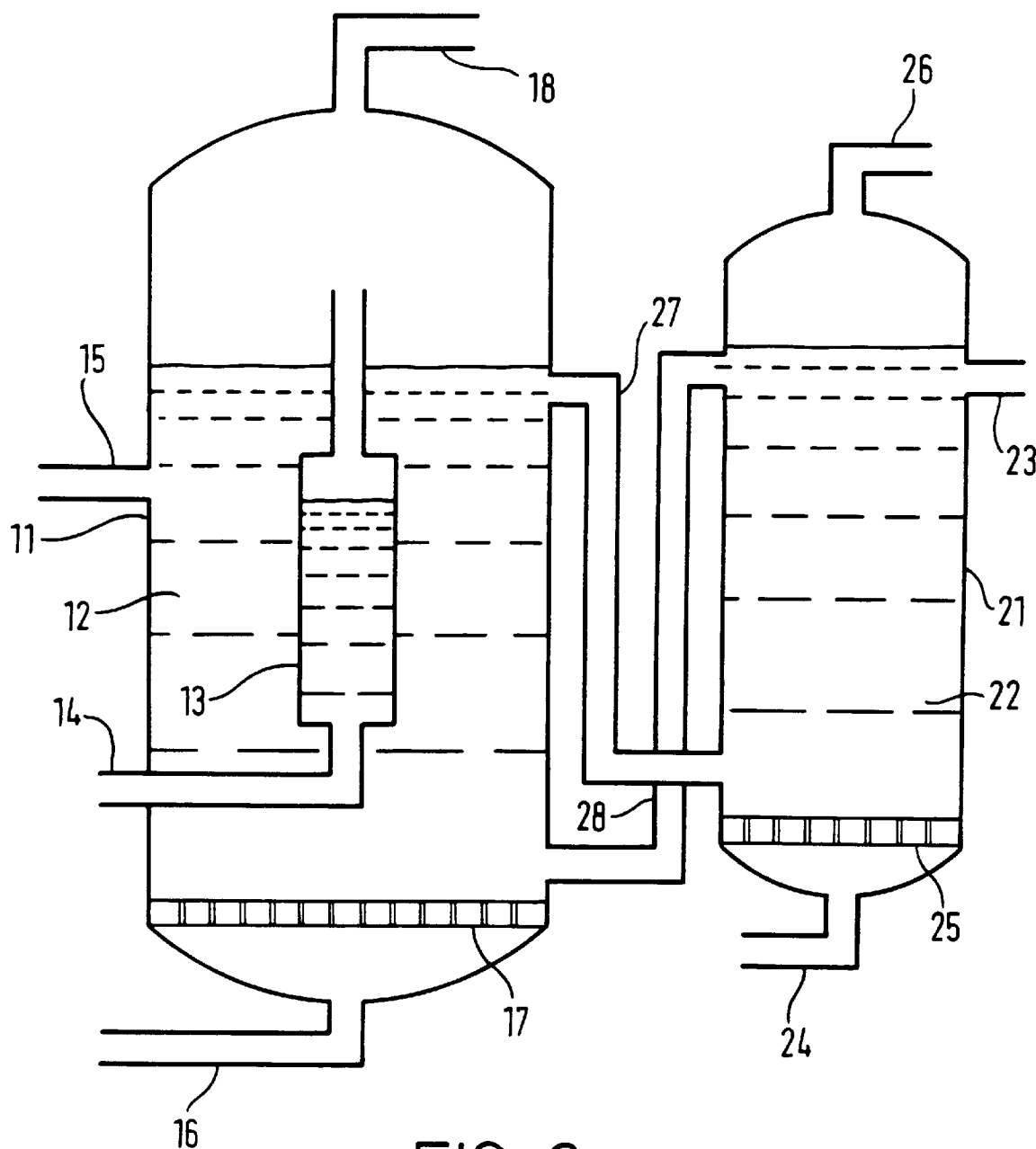
FIG. 2 is a schematic section through a slurry reactor together with a separate regeneration vessel.

FIG. 2 shows an arrangement for carrying out an alternative regeneration method. The reaction vessel 11 is similar to that shown in FIG. 1. There is, however, in addition, a separate regeneration vessel 21. The regeneration vessel 21 contains a slurry 22 of the catalyst in the liquid hydrocarbon product and has a slurry inlet 23, a feed gas inlet 24 at the bottom beneath a gas distribution device 25, and a gas outlet 26 at the top.

The reaction vessel 11 and the regeneration vessel 21 are interconnected by two fluid lines. The first line 27 runs from just below the top of the slurry 12 in the reaction vessel 11 to the bottom of the regeneration vessel 21, just above the distribution device 25. The second line 28 runs from just below the top of the slurry 22 in the regeneration vessel 22 to the bottom of the reaction vessel 11, just above the gas distribution device 17.

In use, the reaction vessel 11 operates continuously in synthesis mode in the same way as the reaction vessel 11 in FIG. 1 when in synthesis mode. However, in the embodiment of FIG. 2, synthesis gas under regeneration conditions is fed to the regeneration vessel 21 by way of the inlet 24 and distribution device 25. Again, the gas is introduced into the slurry 22 as fine streams of bubbles which maintain the slurry in a constant state of agitation.

The catalyst present in the slurry 22 is subjected to regeneration conditions and any unreacted gas (particularly $H_2$ and $CO_2$) is removed by way of the outlet 26. Thus, the regeneration vessel 21 can be considered to function in a similar manner to the reaction vessel 11 when in regeneration mode.

The presence of the fluid lines 27, 28 ensures a constant transfer of slurry 12 containing partially de-activated catalyst from the reaction vessel 11 to the regeneration vessel 21 (line 27) and at the same time, a constant transfer of slurry 22 containing regenerated catalyst from the regeneration vessel 21 to the reaction vessel 11 (line 28). The degree of regeneration can be controlled by adjusting the residence time of the slurry 22 in the regeneration vessel 21. In this way, the catalyst used in the synthesis reaction is constantly regenerated.

The apparatus shown in FIG. 2 can also be operated on a batch basis. In this case, a portion of the slurry 12 including de-activated catalyst is removed from the reaction vessel 11 and transferred to the regeneration vessel 21. Regeneration is then carried out as described above and when complete, the slurry 22, including the regenerated catalyst is returned to the reaction vessel 11. This system offers potential advantages that the degree of regeneration for any batch will be uniform and adjustment is easier to perform.

The invention will now be further illustrated with the following Examples.

EXAMPLE 1

Fischer-Tropsch synthesis was carried out with a 12% Co and 0.5% Re on alumina catalyst at 220° C. and 20 bar (2MPa) total synthesis gas pressure in a continuous slurry stirred tank reactor (CSTR). The reactor volume was 2 liter of which slurry occupied a half. The initial stable hydrocarbon activity was set to the relative activity number 1. At this point the Co conversion was 63%.

The relative activity is defined as the measured rate divided by an estimated rate at the same conditions. To bring the initial activity level to one, the initial relative activity is used as the normalising factor, ie. the relative activity numbers are divided by the initial relative activity.

After a few days of operation the catalyst activity had dropped to a relative activity number of 0.69. The synthesis gas inlet $H_2/CO$ ratio was 2:1. The CO conversion was 68% at a flow rate of 2100 Nl/kgcat/h. The $C_{5+}$ selectivity was 89.4%. The conversion level was then increased to 88% by reducing the flow rate to 1050 Nl/kgcat/h. The $C_{5+}$ selectivity was 89.9%. The exit $H_2/CO$ was close to 2:1.

The catalyst was brought to the regeneration mode by reducing the flow rate and thus increasing the CO conversion. The change to the regeneration mode occurred when the flow rate was reduced to 750 Nl/kgcat/h. The CO conversion stabilised at 99%. The exit CO partial pressure fell to below 0.2 bar (20 kPa) and the exit $H_2/CO$ ratio increased to 14:1. The $C_{5+}$ selectivity dropped to about 60%.

The regeneration mode was maintained for 10 hours after which the system was brought back to the Fischer-Tropsch mode by increasing the flow rate back to 2100 Nl/kgcat/h. The reaction was allowed to continue until the $C_{5+}$ selectivity had increased to over 88%. The relative activity at these final Fischer-Tropsch conditions was 0.77.

EXAMPLE 2

The Fischer-Tropsch synthesis was carried out in the same CSTR as in Example 1 with a 20% Co, 1% Re and 1% Re on alumina catalyst. The temperature was 220° C. and the total synthesis gas pressure 20 bar (2 MPa). Initially the inlet synthesis gas ratio was 2:1.

After a test period, the synthesis gas reaction was set to run 77% CO conversion. Before this the catalyst had deactivated from a relative activity number of 1 to a level of 0.72. At this point the $C_{5+}$ selectivity was 84%. The exit $H_2/CO$ ratio was 1.8:1.

The synthesis gas ratio was increased from 2 to 2.15. This brought a change in the reaction mode. The CO conversion increased to an almost 100% conversion. The $H_2/CO$ ratio at the reactor exit was about 30:1. The CO partial pressure was down to 0.1 bar (10 kPa). The $C_{5+}$ selectivity dropped to about 50%.

The reaction was allowed to continue for 24 hours in the regeneration mode. After this the flow rate was increased to bring the CO conversion down to 57% CO conversion. The synthesis gas ratio was kept constant at 2.15. The catalyst activity was brought back to the initial level, and the FT synthesis proceeded.

We claim:

1. A method for the regeneration of a solid particulate catalyst used in the synthesis of hydrocarbons from synthesis gas in a reaction zone, characterised in that the method comprises: adjusting the feed parameters of the synthesis gas to increase conversion of CO in the synthesis gas until the $H_2/CO$ ratio of the gas leaving the reaction zone exceeds a regeneration mode level of 10:1; maintaining the conversion in the regeneration mode for a period of time in order to reach a predetermined degree of regeneration: and then readjusting the feed parameters for normal operation of the synthesis reaction.

2. A method as claimed in claim 1, wherein the $H_2/CO$ ratio is greater than 20:1.

3. A method as claimed in claim 1, wherein the $H_2/CO$ ratio is greater than 30:1.

4. A method as claimed in claim 1, wherein the step of adjusting the synthesis gas feed parameters comprises reducing the feed rate.

5. A method as claimed in claim 1 wherein, as a result of the increase in the CO conversion rate, the reaction regime to which the synthesis gas is subjected moves from a Fischer-Tropsch synthesis towards a water gas shift reaction.

6. A method as claimed in claim 1, wherein the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

7. A method as claimed in claim 1 wherein the synthesis reaction is carried out in a reaction vessel and a separate regeneration vessel is provided, the vessels being interconnected to allow a slurry of the catalyst and hydrocarbon product to flow from the reaction vessel to the regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

8. A method as claimed in claim 1 wherein the synthesis reaction is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

9. A method as claimed in claim 2 wherein the step of adjusting the synthesis gas feed parameters comprises reducing the feed rate.

10. A method as claimed in claim 3 wherein the step of adjusting the synthesis gas feed parameters comprises reducing the feed rate.

11. A method as claimed in claim 2 wherein, as a result of the increase in the CO conversion rate, the reaction regime to which the synthesis gas is subjected moves from a Fischer-Tropsch synthesis towards a water gas shift reaction.

12. A method as claimed in claim 3 wherein, as a result of the increase in the CO conversion rate, the reaction regime to which the synthesis gas is subjected moves from a Fischer-Tropsch synthesis towards a water gas shift reaction.

13. A method as claimed in claim 4 wherein, as a result of the increase in the CO conversion rate, the reaction regime to which the synthesis gas is subjected moves from a Fischer-Tropsch synthesis towards a water gas shift reaction.

14. A method as claimed in claim 2, wherein the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

15. A method as claimed in claim 3, wherein the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

16. A method as claimed in claim 4, wherein the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

17. A method as claimed in claim 5, wherein the synthesis reaction is carried out in a reaction vessel and the synthesis gas feed parameters to the reaction vessel are adjusted for a predetermined time during which the contents of the reaction vessel are subjected to reducing conditions, the synthesis gas feed parameters then being adjusted back to provide the required conditions for the synthesis of hydrocarbons, whereby the catalyst is regenerated cyclically.

18. A method as claimed in claim 2, wherein the synthesis reaction is carried out in a reaction vessel and a separate regeneration vessel is provided, the vessels being interconnected to allow to slurry of the catalyst and hydrocarbon product to flow from the reaction vessel to regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

19. A method as claimed in claim 3, wherein the synthesis reaction is carried out in a reaction vessel and a separate regeneration vessel is provided, the vessels being interconnected to allow to slurry of the catalyst and hydrocarbon product to flow from the reaction vessel to regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

20. A method as claimed in claim 4, wherein the synthesis reaction is carried out in a reaction vessel and a separate regeneration vessel is provided, the vessels being interconnected to allow to slurry of the catalyst and hydrocarbon product to flow from the reaction vessel to regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

21. A method as claimed in claim 5, wherein the synthesis reaction is carried out in a reaction vessel and a separate regeneration vessel is provided, the vessels being interconnected to allow to slurry of the catalyst and hydrocarbon product to flow from the reaction vessel to regeneration vessel and from the regeneration vessel to the reaction vessel, and in which synthesis gas is fed to the regeneration vessel at parameters which are adjusted to cause reducing conditions within the regeneration vessel whereby the catalyst is regenerated continuously.

22. A method as claimed in claim 2, wherein the synthesis reaction is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

23. A method as claimed in claim 3, wherein the synthesis reaction is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

24. A method as claimed in claim 4, wherein the synthesis reaction is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

25. A method as claimed in claim 5, wherein the synthesis reaction is carried out in a reaction vessel and a separate regeneration vessel is provided, the vessels being interconnected and in which a slurry of the catalyst and hydrocarbon product is transferred to the regeneration vessel, synthesis gas is fed to the regeneration vessel, and the slurry is transferred back to the reaction vessel whereby the catalyst is regenerated batchwise.

* * * * *